US010365665B2

(12) United States Patent
Laible

(10) Patent No.: US 10,365,665 B2
(45) Date of Patent: Jul. 30, 2019

(54) AUTOMATIC DETECTION SYSTEM FOR DETECTING DISRUPTIONS IN THE FLOW TO A DISPENSING APPARATUS

(71) Applicant: Rodney Laible, Omaha, NE (US)

(72) Inventor: Rodney Laible, Omaha, NE (US)

( * ) Notice: Subject to any disclaimer, the term of this patent is extended or adjusted under 35 U.S.C. 154(b) by 0 days.

(21) Appl. No.: 16/136,588

(22) Filed: Sep. 20, 2018

(65) Prior Publication Data
US 2019/0018431 A1 Jan. 17, 2019

Related U.S. Application Data

(63) Continuation-in-part of application No. 15/443,106, filed on Feb. 27, 2017.

(60) Provisional application No. 62/447,124, filed on Jan. 17, 2017.

(51) Int. Cl.
| B65B 57/18 | (2006.01) |
| G05D 7/06 | (2006.01) |
| G01N 21/85 | (2006.01) |
| B67D 7/62 | (2010.01) |
| B67D 7/56 | (2010.01) |

(52) U.S. Cl.
CPC ............ G05D 7/0617 (2013.01); B65B 57/18 (2013.01); B67D 7/565 (2013.01); B67D 7/62 (2013.01); G01N 21/85 (2013.01)

(58) Field of Classification Search
CPC .......... B65B 57/18; B67D 7/565; B67D 7/62; G08B 7/06; G01N 21/85
See application file for complete search history.

(56) References Cited

U.S. PATENT DOCUMENTS

| 5,277,175 A | * | 1/1994 | Riggs ................ A61M 16/162 128/200.19 |
| 7,028,724 B2 | | 4/2006 | Cohen et al. |
| 7,059,363 B2 | | 6/2006 | Sugiyama et al. |
| 7,694,691 B2 | | 4/2010 | Wodjenski et al. |
| 8,182,462 B2 | | 5/2012 | Istoc et al. |
| 9,586,306 B2 | | 3/2017 | Zhang et al. |
| 2005/0005994 A1 | | 1/2005 | Sugiyama et al. |
| 2012/0101474 A1 | | 4/2012 | Istoc et al. |
| 2014/0045409 A1 | | 2/2014 | Zhang et al. |

* cited by examiner

Primary Examiner — Nicolas A Arnett
(74) Attorney, Agent, or Firm — Dennis L. Thomte; Thomte Patent Law Office LLC

(57) ABSTRACT

An automatic detection system is provided for detecting disruptions in the flow of liquid from a liquid container or containers to a dispensing apparatus. Two embodiments of the system are disclosed. In the first embodiment, a single liquid container is utilized. In the second embodiment, two liquid containers are utilized. In both embodiments, an optical sensor is employed to detect a disruption in the flow of liquid from the liquid containers to the dispensing apparatus.

20 Claims, 4 Drawing Sheets

AUTOMATIC DETECTION SYSTEM FOR DETECTING DISRUPTIONS IN THE FLOW TO A DISPENSING APPARATUS

CROSS REFERENCE TO RELATED APPLICATION

This is a Continuation-in-Part application of application Ser. No. 15/443,106, filed Feb. 27, 2017, entitled AN AUTOMATIC DETECTION SYSTEM FOR DETECTING DISRUPTIONS IN THE FLOW TO A DISPENSING APPARATUS, which claims priority from the Provisional Patent Application Ser. No. 62/447,124 filed Jan. 17, 2017 entitled AN AUTOMATIC DETECTION SYSTEM FOR DETECTING DISRUPTIONS IN THE FLOW TO A DISPENSING APPARATUS.

BACKGROUND OF THE INVENTION

Field of the Invention

This invention relates to an automatic detection system for detecting disruptions in the flow of liquid to a dispensing apparatus. Even more particularly, this invention relates to an automatic detection system which detects an interruption of the flow of liquid to a dispensing apparatus and which includes a visual alarm, an audio alarm, or a data alarm which are activated when the flow of liquid to a dispensing apparatus has been disrupted.

More particularly, this invention relates to an automatic detection system which includes an optical sensor which detects an interruption of the flow of liquid and which detects a change in the flow of liquid to a dispensing apparatus and which includes a visual alarm, an audio alarm, or a data alarm which are activated when the flow of liquid to a dispenser apparatus has been corrupted or changed.

Description of the Related Art

There are many situations where it is desired to dispense liquid chemicals or other liquids into a receptacle having water or other liquid therein. There are also other situations where it is desirable to mix the liquid chemicals with water prior to the mixture being discharged into a receptacle. There are also situations wherein both of the above methods are required to be performed at one station where there is a need for injecting liquid chemicals into a first receptacle having water or other liquid therein and there is a need for mixing liquid chemicals with water prior to being discharged into another receptacle.

In each of those situations, the liquid chemicals are in a container such as a bottle with the chemicals being drawn therefrom by a pump or other means. Usually, the liquid chemical containers are not closely monitored as to the amount of liquid chemical remaining in the liquid chemical container. If the liquid chemical container becomes empty, the proper amount of chemical will not be supplied to the receptacle. Further, if the pumps run empty, they may become damaged.

There is therefore a need to provide an electronic detection system which includes an alarm which may audibly, visually or data indicate that the liquid chemical container is empty or some other disruption in the flow has occurred. There is also a need for remotely controlling the systems by way of a computer, a lap top, a tablet or a cell phone.

The co-pending application Ser. No. 15/443,106 filed Feb. 27, 2017 entitled AN AUTOMATIC DETECTION SYSTEM FOR DETECTING DISRUPTIONS IN THE FLOW TO A DISPENSING APPARATUS represents an improvement in the art. The instant invention represents a further improvement in the art.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

Two embodiments of an automatic detection system for detecting disruptions in the liquid flow to a dispensing apparatus are disclosed. In the first embodiment, the system has a valve module preferably positioned on a vertically disposed support with the valve module having a first liquid inlet port, a first liquid outlet port, and an electrically operated first valve, which is movable between closed and open positions, positioned between the first liquid intake port and the first liquid outlet port. A first liquid container, such as a bottle, is provided which has a liquid outlet with the first liquid container being spaced from the valve module and with the liquid outlet of the first liquid container being in fluid communication with the first liquid intake port of the valve module.

An alarm module is also provided in the first embodiment which is remotely positioned from the valve module. The alarm module includes an optical sensor, a visual alarm, an audible alarm, and a data alarm. The optical sensor includes an optical tube extending therethrough which has an intake end and an outlet end. The optical sensor includes an emitter at one side of the optical tube and a receiver at the other side of the optical tube. The first liquid outlet port of the valve module is fluidly connected to the intake end of the optical tube in the optical sensor. The outlet end of the optical tube of the optical sensor is fluidly connected to the intake end of a pump for drawing liquid from the first liquid container through the first valve of the valve module, when the first valve of the valve module is in its open position, through the optical tube in the optical sensor, through the pump and into a remote receptacle. When the optical sensor senses a disruption of liquid flowing through the optical tube thereof, the alarms will be activated. A computer driven controller is provided which controls the operation of the valve module, the optical sensor, the alarm module and the pump.

It is therefore a principal object of the invention to provide an automatic detection system which detects disruptions in the flow to a dispensing apparatus.

A further object of the invention is to provide an automatic detection system which detects disruptions in the flow to a dispensing apparatus with the system including an audible alarm, a visual alarm, or a data alarm which indicates that there has been a disruption in the flow of liquid to a dispensing apparatus.

Yet another object of the invention is to provide an automatic detection system of the type described wherein the dispensing system is computer controlled.

Still another object of the invention is to provide an automatic detection system of the type described wherein the chemicals in containers may be drawn therefrom by a peristaltic pump, a piston pump, a hydraulic pump, other types of pumps, or a Venturi apparatus.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

Figure 1:
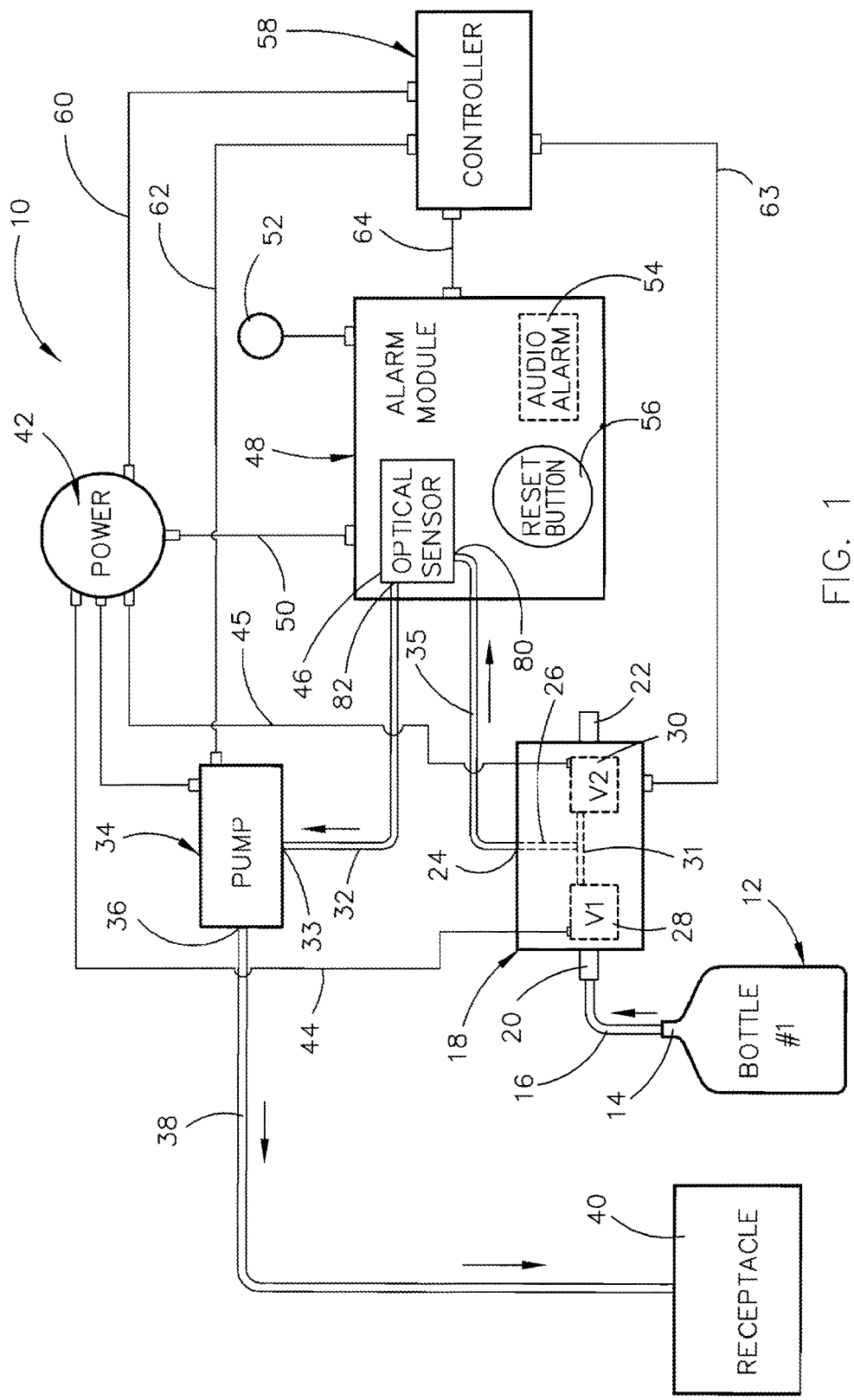
FIG. 1 is a schematic of the first embodiment of the invention.

The first embodiment of the automatic detection system for detecting disruptions in the flow to a dispensing apparatus is referred to by the reference numeral 10 and is depicted in schematic form in FIG. 1. The numeral 12 refers to a liquid container, such as a bottle, which will usually contain chemicals but could contain other liquids. An insert 14 is inserted into the neck of the container 12 and may be of the type such as shown in my earlier insert patents, namely U.S. Pat. Nos. 9,242,847; 9,126,725; and 8,708,203 the disclosures of which are incorporated herein to complete this disclosure if necessary.

A flexible tube 16 extends from insert 14 of container 12 for supplying liquid to a valve module 18 which is available in the marketplace. Valve module 18 will usually be mounted on a vertically disposed support such as a wall, bracket, etc. Valve module 18 includes a first liquid intake port 20, a second liquid intake port 22, which is not utilized in the FIG. 1 embodiment and a liquid outlet port 24. A short tube 26 has its outlet end in fluid communication with the liquid outlet port 24. It should be noted that the container 12 may be positioned above valve module 18.

Valve module 18 includes an electrically operated valve 28 of conventional design and an electrically operated valve 30 of conventional design, which is not utilized in the FIG. 1 embodiment. The intake end of tube 26 is in fluid communication with the tube 31 which extends between the discharge side of valve 28 and the discharge side of valve 30. As seen, tube 16 is fluidly connected to the first liquid intake port 20 of valve module 18. When valve 28 is in its open position, liquid may pass therethrough so that the liquid is supplied to tube 31, the tube 26 and the outlet port 24. When valve 28 is closed, liquid may not pass therethrough.

A flexible tube 32 has its discharge end thereof fluidly connected to the liquid intake port 33 of pump 34. In this embodiment, the pump 34 is a peristaltic hose pump. However, other pumps such as a radial piston pump, a gear pump, a vane pump, a lobe pump, a piston pump, a Venturi pump, etc., could be used. A flexible tube 35 has its liquid intake end fluidly connected to port 24. The discharge side 36 of pump 34 has a hose, tube or pipe 38 extending therefrom to a receptacle 40 such as a sink, a tub, etc.

The valves 28 and 30 of module 18 are electrically connected to a conventional power source 42 by leads 44 and 45 respectively. The liquid intake end of tube 32 is fluidly connected to an optical sensor 46 positioned within an alarm module 48. The discharge end of tube 35 is fluidly connected to the liquid intake side of sensor 46. Optical sensor 46 will be described in greater detail hereinafter. Although it is preferred that the optical sensor 46 be positioned within alarm module 48, it could be located outside of alarm module 48. Alarm module 48 and optical sensor 46 are electrically connected to the power source 42 by a lead or leads 50. Alarm module 48 includes a visual signal device such as a light 52. Alarm module 48 also includes an audible signaling or warning device 54. Alarm module 48 will usually include a data alarm. Optical sensor 46 and alarm module 48 are configured to activate the devices 52, 54 and the data alarm upon the optical sensor 46 detecting a disruption of liquid flow through sensor 46 as will be described hereinafter. The alarm module 48 also includes a lighted reset button 56.

The numeral 58 refers to a computer driven controller which is electrically connected to the power source 42 by a lead or leads 60. Controller 58 is electrically connected to pump 34 by a lead or leads 62. Controller 58 is electrically connected to valve module 18 by a lead or leads 63. Controller 58 is electrically connected to the alarm module 48 and optical sensor 46 by a lead or leads 64.

Figure 2:
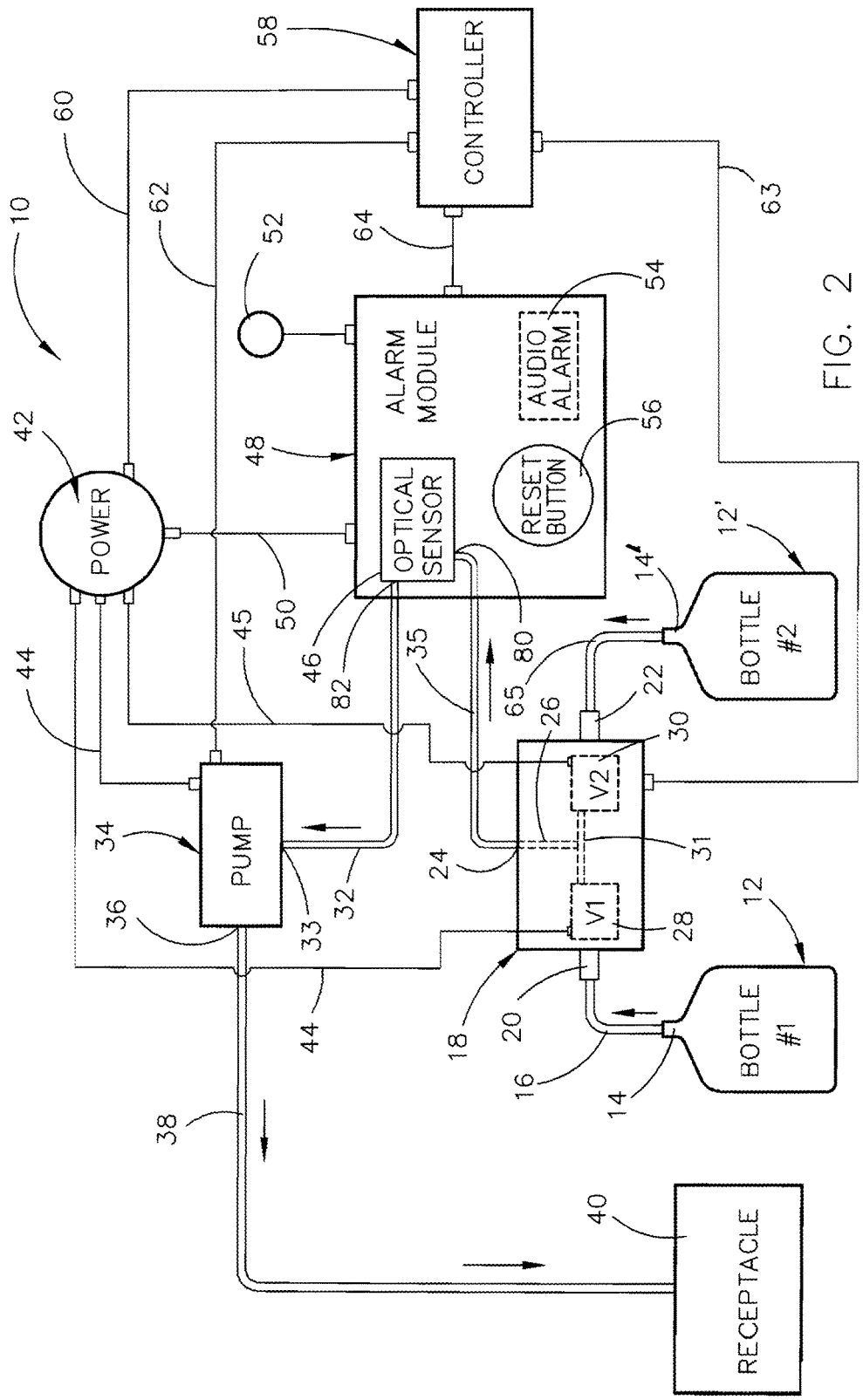
FIG. 2 is a schematic of the second embodiment of the invention.
Figure 3:
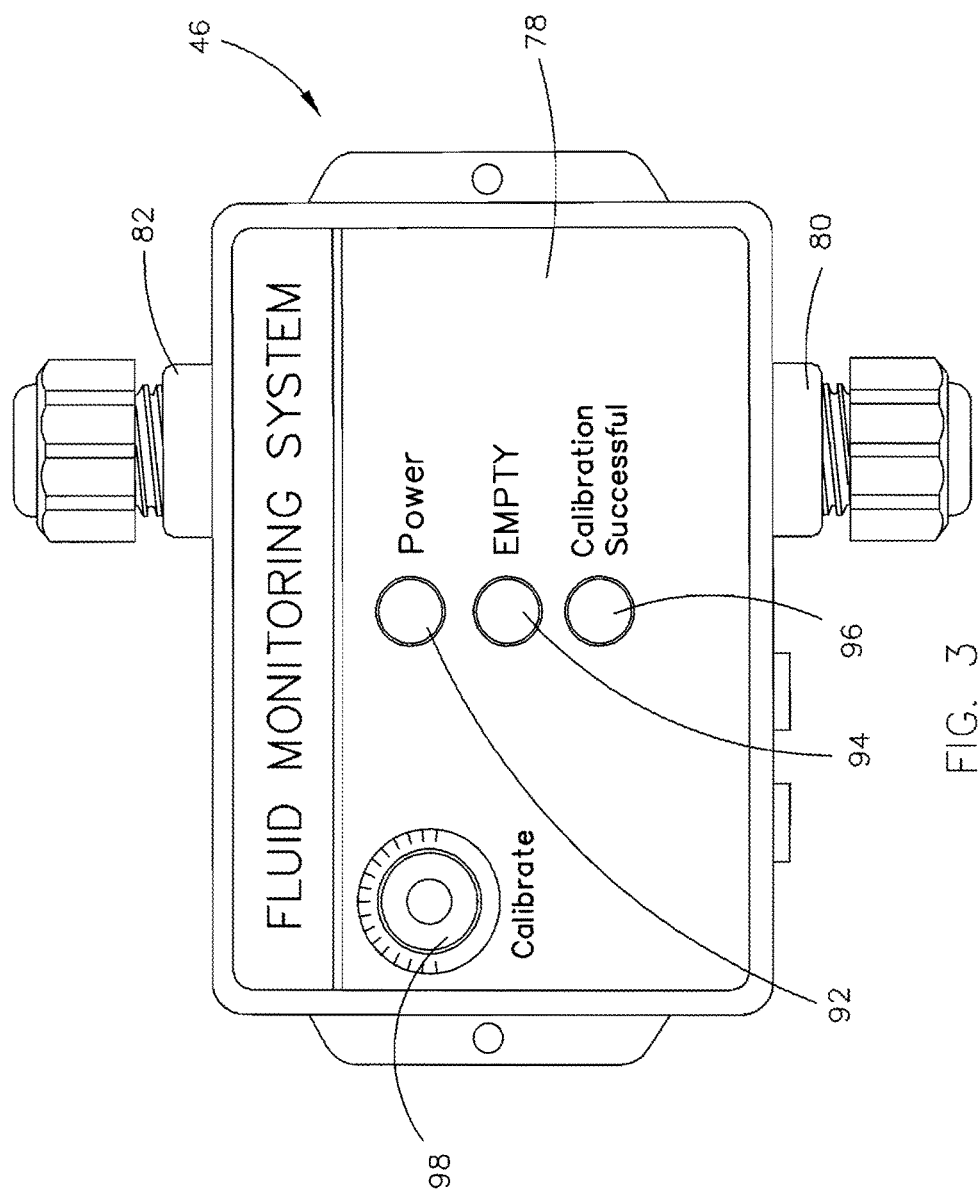
FIG. 3 is a frontal view of the optical sensor of this invention.
Figure 4:
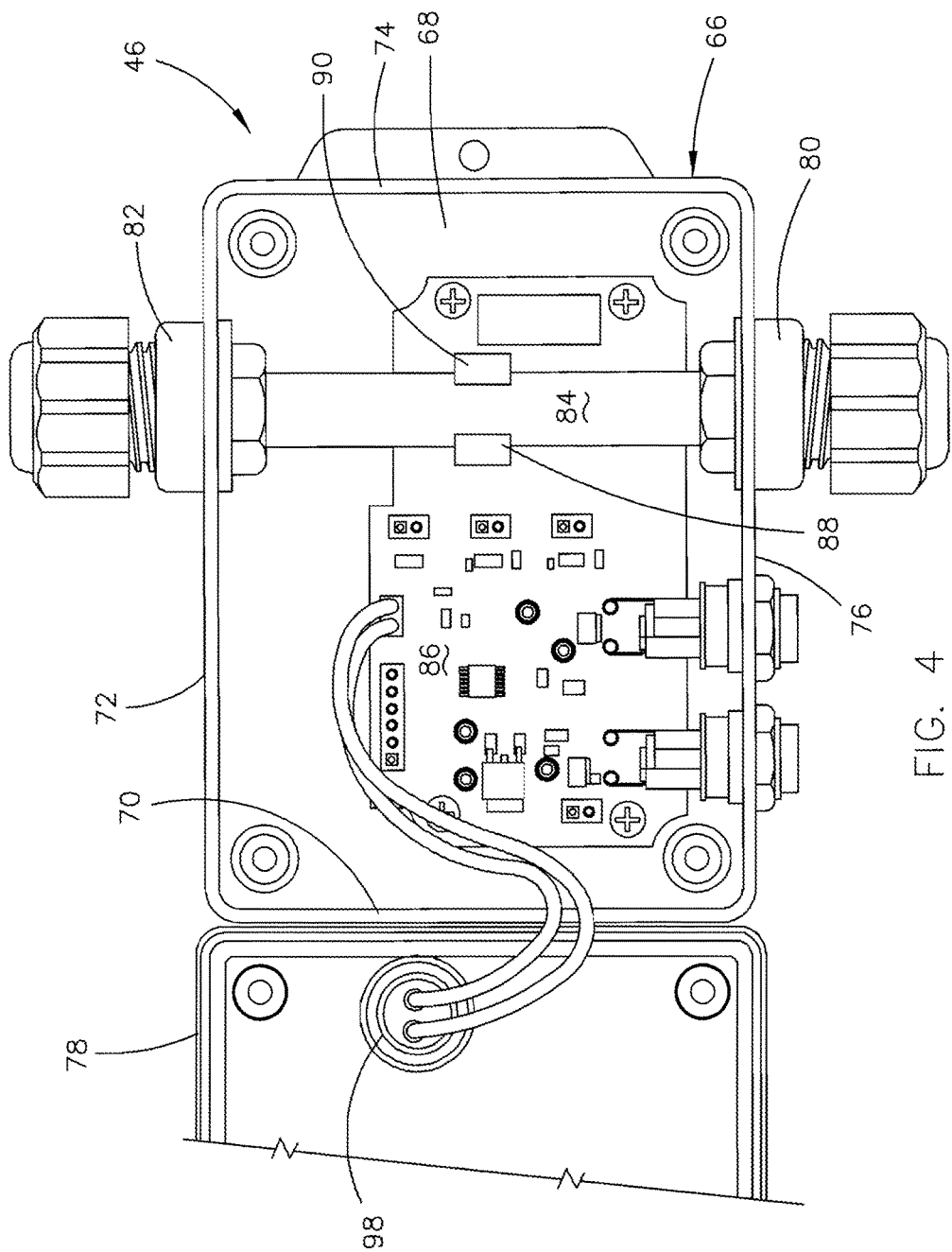
FIG. 4 is a frontal view of the optical sensor with the cover thereof being open.

The second system of FIG. 2 is identical to the system of FIG. 1 except that a second liquid container 12' is utilized. Container 12' is identical to liquid container 12. Container 12' is fluidly connected to the liquid intake port 22 which is fluidly connected to the intake side of valve 30 by tube or pipe 65. It should be noted that the liquid containers 12 and 12' may be positioned above the valve module 18.

Optical sensor 46 will now be described in greater detail. Optical sensor 46 includes a housing or box 66 having an interior 68. Housing 66 includes side walls 70, 72, 74 and 76. A cover 78 selectively closes the front of the housing 66. A liquid inlet fitting 80 is positioned in wall 76 with the fitting 80 being fluidly connected to the discharge end of tube 35. A liquid outlet fitting 82 is positioned in wall 74 with the fitting 82 being fluidly connected to the intake end of tube 32.

The sensor 46 includes an elongated optical tube 84 which has its ends fluidly connected to fittings 80 and 82. Tube 84 is clear or transparent. Sensor 46 includes a circuit board 86 in the interior thereof which is operatively electrically connected to the power source 42 by way of the lead 50. Circuit board 86 includes a transmitter or emitter 88 which extends from circuit board 86. Circuit board 86 also includes a receiver 90 which extends from circuit board 86 and which is spaced from transmitter 88. As seen, the optical tube 84 is positioned between the transmitter 88 and the receiver 90.

The exterior side of cover 78 has a power light 92, an empty light 94, a calibration successful light 96 and a calibration button or knob 98, all of which are electrically connected to the circuit board 86.

The sensor 46 will now be described in more detail. The sensor 46 is manufactured by TT Electronics. The part numbers of the TT Electronics sensor are OP550B and OP240B. Initially, the sensor 46 must be calibrated. The valve 28 is opened by the controller 58. The pump 34 is then actuated so that the liquid from container 12 is drawn through the open valve 28 and through tube 35 into the intake side of sensor 46 and through the optical tube 84. When the optical tube 84 is full, the calibration button 98 is depressed. This causes the system to calibrate the chemical that is being dispensed. After the calibration, the calibration successful light 96 will be lighted. The alarm system will be activated if there is a change in the liquid flow in the optical tube 84. If the optical sensor 46 detects a change in the liquid flow be it bubbles, lack of chemical or different chemicals, the alarm system will be activated. The alarm will continue until the problem is resolved.

The operation of the automatic detection system of FIG. 1 will now be described. A container 12 having the desired liquid therein is placed into position. The controller 58, at predetermined times, will activate alarm module 48, optical sensor 46, module 18, the valve 28 and the pump 34. At that time, valve 28 will be moved to its open position. The operation of the pump 34 draws liquid from the container 12 by way of the tube 16, port 20, valve 28, tube 31, port 24, tube 35, optical sensor 46 and tube 32. The pump 34 discharges the liquid therefrom by way of the discharge side 36 and hose or tube 38 into the receptacle 40. At a predetermined time, as controlled by controller 58, the system will halt the pumping of liquid into the receptacle 40.

If the container 12 becomes empty or some malfunction occurs in the system, the flow of liquid to the pump 34 will be disrupted. When such disruption of flow occurs, the optical sensor 46 will sense the disruption of flow through the optical tube 84. The change in the flow or liquid through the optical tube 84 of optical sensor 46 will cause the visual, data and audible signaling devices to be activated. The controller 58 will then close valve 28 and shut down pump 34. The visual, data and audible devices will alert the operator or attendant that a disruption has occurred. The controller 58 may also alert personnel by cell phone or other means that the disruption has occurred.

The attendant will then place a filled liquid container in place and connect the container to the module 18. The attendant will then press the reset button 56 to restart the system.

The system of FIG. 2 is identical to the system of FIG. 1 except that a second liquid container 12' will be placed into the system. Container 12' is fluidly connected by tube 65 to the second liquid intake port 22 of the module 18 and the valve 30 will become functional. The containers 12 and 12' will normally contain the same liquid but they could contain different liquids. Thus, the controller 58 may place either bottles 12 or 12' into operation. Normally, the container 12 will be in operation before the container 12'. At any time, the controller 58 may switch the system taking one container out of operation and placing the other container into operation.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. An automatic detection system for detecting disruptions in the liquid flow to a dispensing apparatus, comprising:

a valve module;

said valve module having a first liquid inlet port and a first liquid outlet port;

an electrically operated first valve positioned in said valve module;

said first valve having a liquid intake side and a liquid outlet side;

said liquid intake side of said first valve being in fluid communication with said first liquid port of said valve module;

said liquid outlet side of said first valve being in fluid communication with said first liquid outlet port of said valve module;

said first valve being movable between open and closed positions;

a first liquid container having a liquid outlet;

said first liquid container being spaced from said valve module;

said liquid outlet of said first liquid container being in fluid communication with first liquid inlet port of said valve module and said liquid intake side of said first valve;

an alarm module positioned remotely from said valve module;

said alarm module including at least one alarm;

an optical sensor positioned in said alarm module;

said optical sensor having a liquid intake end and a liquid outlet end;

said intake end of said optical sensor being in fluid communication with said first liquid outlet port of said valve module and said liquid outlet side of said first valve;

means spaced from said valve module and said optical sensor for selectively supplying liquid from said first liquid container through said first valve, when said first valve is moved from said closed position to said open position, into said intake end of said optical sensor, through said optical sensor, outwardly through said liquid outlet of said optical sensor, and supplying the liquid to a remote receptacle;

a computer driven controller;

said optical sensor being electrically connected to said computer driven controller;

said computer driven controller controlling the said means for supplying liquid from said first liquid container, said first valve, said optical sensor and said alarm module;

said computer driven controller deactivating said means for supplying liquid when said optical sensor senses a disruption of liquid passing through said optical sensor; and said computer driven controller activating said at least one alarm when said optical sensor senses a disruption of liquid passing through said optical sensor.

2. The automatic detection system of claim 1 wherein said means for supplying liquid from said first liquid container comprises a pump means.

3. The automatic detection system of claim 1 wherein said means for supplying liquid from said first liquid container comprises a Venturi means.

4. The automatic detection system of claim 1 wherein said means for supplying liquid from said first liquid container comprises a radial piston pump.

5. The automatic detection system of claim 1 wherein said means for supplying liquid from said first liquid container comprises a gear pump.

6. The automatic detection system of claim 1 wherein said means for supplying liquid from said first liquid container comprises a vane pump.

7. The automatic detection system of claim 1 wherein said means for supplying liquid from said first liquid container comprises a peristaltic hose pump.

8. The automatic detection system of claim 1 wherein said means for supplying liquid from said first liquid container comprises a lobe pump.

9. The automatic detection system of claim 1 wherein said means for supplying liquid from said first liquid container comprises a piston pump.

10. The automatic detection system of claim 1 wherein said alarm module includes a reset button.

11. An automatic detection system for detecting disruptions in the flow to a dispensing apparatus, comprising:
   a valve module;
   said valve module having a first liquid outlet port, a first liquid intake port, a second liquid intake port, an outlet port, a normally closed electrically operated first valve positioned between said first liquid intake port and said first liquid outlet port and a normally closed electrically operated second valve positioned between said second liquid intake port and said first liquid outlet port;
   each of said first and second valves being movable between open and closed positions;
   a first liquid container having a liquid outlet;
   said first liquid container being spaced from said valve module;
   said liquid outlet of said first liquid container being in fluid communication with said first liquid intake port of said valve module;
   a second liquid container having a liquid outlet;
   said second liquid container being spaced from said valve module;
   said liquid outlet of said second liquid container being in fluid communication with said second liquid intake port of said valve module;
   an alarm module positioned remotely from said valve module;
   an optical sensor positioned in said alarm module;
   said optical sensor having a liquid intake end and a liquid outlet end;
   said intake end of said optical sensor being in fluid communication with said first liquid outlet port of said valve module and said liquid outlet side of said first valve;
   said outlet port of said valve module being in communication with said fluid inlet end of said optical sensor;
   said alarm module including at least one of a visual alarm, a data alarm and an audible alarm;
   said at least one of said visual alarm, said data alarm and said audible alarm being activated upon the flow of liquid from said first liquid container to said valve module being disrupted;
   said at least one of said visual alarm, said audible alarm and said data alarm being activated upon the flow of liquid from said liquid outlet of said second liquid container to said second liquid inlet port of said valve module being disrupted;
   means for selectively supplying liquid from said first liquid container through said first valve, when said first valve is moved from its closed position to its open position, and through said first liquid output port of said valve module, through said optical sensor, through said means for supplying liquid and supplying the liquid to a remote receptacle;
   said means for selectively supplying liquid from said first liquid container also being configured to selectively supply liquid from said second liquid container through said second valve, when said second valve is moved from its closed position to its open position, and through said first liquid output port of said valve module through said optical sensor, through said means supplying the liquid to a remote receptacle;
   and a computer driven controller which controls the operation of said means for supplying liquid from said first and second liquid containers, said first and second valves, said optical sensor and said alarm module.

12. The automatic detection system of claim 11 wherein said means for supplying liquid from said first and second liquid containers comprises a pump means.

13. The automatic detection system of claim 11 wherein said means for supplying liquid from said first and second liquid containers comprises a radial piston pump.

14. The automatic detection system of claim 11 wherein said means for supplying liquid from said first and second liquid containers comprises a gear pump.

15. The automatic detection system of claim 11 wherein said means for supplying liquid from said first and second liquid containers comprises a vane pump.

16. The automatic detection system of claim 11 wherein said means for supplying liquid from said first and second liquid containers comprises a peristaltic hose pump.

17. The automatic detection system of claim 11 wherein said means for supplying liquid from said first and second liquid containers comprises a lobe pump.

18. The automatic detection system of claim 11 wherein said means for supplying liquid from said first and second liquid containers comprises a piston pump.

19. The automatic detection system of claim 11 wherein said means for supplying liquid from said first and second liquid containers comprises a Venturi pump.

20. The automatic detection system of claim 11 wherein said alarm module includes a reset button.

* * * * *